US005977335A

United States Patent [19]

Kim et al.

[11] Patent Number: 5,977,335

[45] Date of Patent: Nov. 2, 1999

[54] **DNA ENCODING AMARANDIN-S RIBOSOME INACTIVATING PROTEIN OF *AMARANTHUS VIRIDIS***

[75] Inventors: Yong Sig Kim; Sun Chung Park; Soo Kyung Oh; Jeong Woo Cho; Chang H. Chung, all of Kwangju, Rep. of Korea

[73] Assignee: Korea Kumho Petrochemical Co., Ltd., Seoul, Rep. of Korea

[21] Appl. No.: 09/069,330

[22] Filed: Apr. 29, 1998

Related U.S. Application Data

[63] Continuation-in-part of application No. 08/916,444, Aug. 22, 1997, abandoned.

[51] Int. Cl.$^{6}$ .................................................. C12N 15/29

[52] U.S. Cl. .................... 536/23.6; 435/320.1; 435/471; 435/252.3

[58] Field of Search ....................... 536/23.6; 435/320.1, 435/471, 252.3

[56] References Cited

U.S. PATENT DOCUMENTS 5,501,970 3/1996 Legname et al. .

5,529,932 6/1996 Lorenzetti et al. .

OTHER PUBLICATIONS

Hudson, J.B., *Antiviral Compounds from Plants,* 1990 CRC Press, Inc., pp. 167–177.

Turpen, T.H., *BioTechniques,* "Rapid Isolation of RNA by a Guanidinium Thiocyanate/Cesium Chloride Gradient Method", 4:1, 1986.

Hung, et al., *J. Mol. Biol.,* 1993, 229:263–267.

Krawetz, S., et al., *BioTechniques,* Nov./Dec. 1984, pp. 342–347.

*J. Mol. Biol.,* 229, 1993, 263–267.

*Primary Examiner*—Elizabeth F. McElwain
*Assistant Examiner*—Ousama Zaghmont
*Attorney, Agent, or Firm*—Kenyon & Kenyon

[57] ABSTRACT

A CDNA clone encoding amarandin-S, a eukaryotic ribosome-inactivating protein (RIP) having antiviral activity is disclosed. Also disclosed are hybrid vectors encoding the cDNA and host cells transformed with the vector.

6 Claims, 3 Drawing Sheets

| ENZYME | POSITION | ENZYME | POSITION | ENZYME | POSITION |
|---|---|---|---|---|---|
| AccI | 306 951 | AflI | 243 408 | AluI | 7 728 752 |
| AlwI | 12 | AocI | 6 535 | AosI | 226 |
| ApyI | 399 411 477 | AseI | 957 | AspI | 464 |
| AsuI | 243 408 | BanI | 849 | BanII | 6 |
| BclI | 118 | BglI | 577 | BsmAI | 237 |
| BsmI | 635 | Bsp1286I | 6 535 | BspHI | 115 |
| BstBI | 171 | BstNI | 399 411 477 | BstXI | 664 |
| CfoI | 227 586 | CfrI | 661 | ClaI | 14 |
| DdeI | 239 424 814 832 | DpnI | 13 119 963 | DraI | 263 |
| DraII | 242 | Eco57I | 142 | EcoRI | 188 |
| EcoRV | 713 | Fnu4HI | 357 684 | FspI | 226 |
| GdiII | 661 | HaeI | 396 413 | HaeIII | 397 414 662 |
| HgiAI | 6 535 | HinPII | 227 586 | HincII | 387 |
| HinfI | 17 169 426 444 545 775 | HphI | 185 | KpnI | 849 |
| Ksp632I | 838 | Ksp632I | 40 | MaeI | 348 579 772 |
| MaeII | 467 689 858 | MseI | 133 264 592 694 958 | MstI | 226 |
| NlaIII | 82 98 116 256 701 | NlaIV | 243 849 | Nsp(7524)I | 255 |
| NspII | 6 535 | PleI | 426 | PpuMI | 242 |
| RsaI | 160 203 345 698 850 905 | | | SacI | 6 |
| Sau3AI | 13 119 963 | ScaI | 344 904 | SecI | 476 |
| SnaBI | 857 | SnaI | 951 | SplI | 159 |
| SstIII | 467 689 858 | TaqI | 15 172 548 | TspEI | 175 189 210 261 322 513 622 732 896 911 |

FIG.2

SEQUENCE LISTING

```
<160> NUMBER OF SEQ ID NOS: 3

<210> SEQ ID NO 1
<211> LENGTH: 852
<212> TYPE: DNA
<213> ORGANISM: Amaranthus Viridis

<400> SEQUENCE: 1

atgaagaagg ttttaggagg aggaacatgg gtttggtggt gcatgataat gcttattatc     60

atgatcacta ccgtagttaa gcaatctgaa gcacaacaat atcgtacggt gggattcgaa    120

ttacataaag agaattcacc aaatgggtac gcaaatttct tgagaaggtt gcgcagtgca    180

gtctcaggtc ccacaagagc atgtaattta aacattacac aaagtaatcc accaatagac    240

agagaatatg tctacataag gctacaattt agcgacacac aatgggtagt actaggaatg    300

gctgccaaag atatgtatat ttggggttat gttgacaata ggccaggctt cggaccaggc    360

caaccacctg agtcaaactt cctaatggat tctccgccag aagcacgaca acgtcttttc    420

ccaggttcta acagaagaat aacagattac ggaggaaatt acaacagtct tcaacaaaga    480

gcacaaagga atcgagataa tgttccattg ggactgacaa gcctagacgg cgcacttaaa    540

agcgtgtatg gaaaatcaac ttcacaattg aatgaaggga atgcagaagc aagatttttt    600

cttacggcca tccaaatggt tgcagaagca gcacgtttta agtacatgga gagagggata    660

tcagcaccac cagctaattt tagacaaaat atgatagctt tccaaaatgg ttgggctaga    720

atctctactc ttatacataa tgcagaaggg gctactccta agtgtcaggc ttttcctcag    780

cctcttcgta ttggtaccct tacgtatgga aatgtcaatg agataaggaa tgagattgga    840

attatcaagt ac                                                        852


<210> SEQ ID NO 2
<211> LENGTH: 24
<212> TYPE: DNA
<213> ORGANISM: Amaranthus Viridis

<400> SEQUENCE: 2

atgaagaagg ttttaggagg agga                                            24
```

-continued

```
<210> SEQ ID NO 3
<211> LENGTH: 23
<212> TYPE: DNA
<213> ORGANISM: Amaranthus Viridis

<400> SEQUENCE: 3

gaggcagcrm grttcaagta cat                                      23
```

DNA ENCODING AMARANDIN-S RIBOSOME INACTIVATING PROTEIN OF *AMARANTHUS VIRIDIS*

CROSS REFERENCE TO RELATED APPLICATION

This application is a continuation-in-part of pending application Ser. No. 08/916,444 filed Aug. 22, 1997, which is incorporated herein in its entirety by reference.

BACKGROUND OF THE INVENTION

The present invention relates to the isolated cDNA sequence encoding amarandin-S, eukaryotic ribosome-inactivating protein (RIP) having antiviral activity, which is present in *Amaranthus viridis*, to the expression vector containing said cDNA sequence and to a host transformed by said vector.

An interesting recent development is the discovery of plant proteins that have prophylactic effects against viruses. According to *Antiviral Compounds from Plants*, 1st ed., CRC Press, Inc., (1990), ribosome-inactivating proteins (RIPs) are plant toxins, classified as type 1 and 2, having antiviral and abortifacient activities with N-glycosidase activity on ribosomal RNA sequence. Interest in ribosome-inactivating proteins stems from their potential utilization in medicine and agriculture, due to their antiviral and antifungal activities. Also, efforts have been made either to inhibit virus replication comprising virus-induced human diseases, like HIV-1 replication, selectively in cell cultures or to custom design extremely specific and very effective small peptide conferring an antiviral activity to interfere with the penetration stage of certain myxoviruses.

SUMMARY OF THE INVENTION

It is an object of the present invention to isolate cDNA sequence that encodes antiviral protein amarandin-S of *A. viridis.*

It is another object of the present invention to provide the expression vector containing said cDNA sequence.

It is still another object of the present invention to provide a transformed host that contains said cDNA sequence or said expression vector and is capable of expressing said cDNA sequence.

In accordance with a further object of the present invention, there has been provided the expression vector comprising cDNA sequence as above, said vector being capable of being transferred to and replicating in a host.

In accordance with yet a further object of the present invention, there has been provided the expression vector as above, said vector being plasmid pLES97010.

In accordance with another object of the present invention, there has been provided a transformed host, *E. coli* strain BL21(DE3), comprising said expression vector or said cDNA sequence as above, said host being capable of expressing said cDNA sequence.

Further advantages, objects and features of the present invention will become apparent from the following detailed description. It should be understood, however, that the detailed description, while indicating preferred embodiments of the invention, is giving by way of illustration only, since various changes and modifications within the spirit and the scope of the invention will become apparent to those skilled in the art from this detailed description.

BRIEF DESCRIPTION OF THE DRAWING

FIG. 2 is a diagram of the restriction map of the isolated nucleotide sequence of amarandin-S cDNA of *A. viridis*, 852 base pairs of maximum open reading frame in length.

DETAILED DESCRIPTION OF THE PREFERRED EMBODIMENTS

Figure 1:
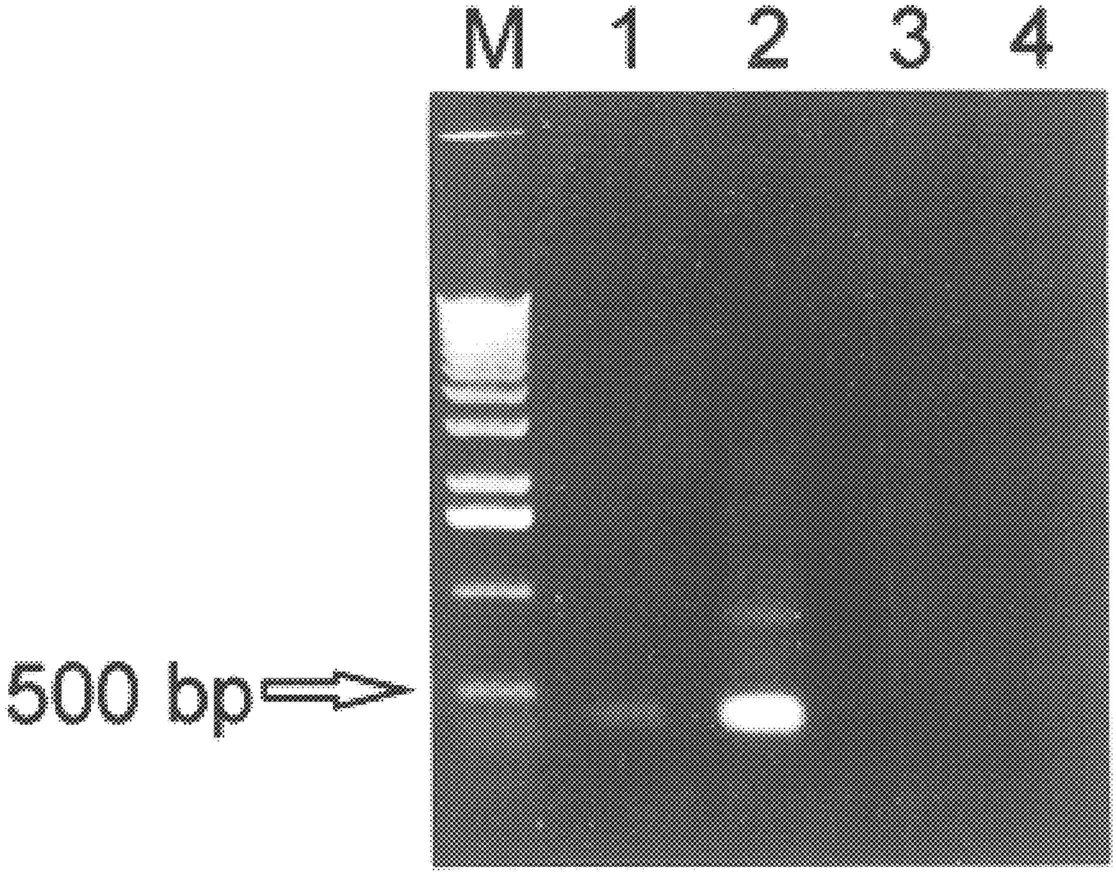
FIG. 1 is EtBr stained 1.0% Agarose gel electrophoresed PCR products of amarandin-S, antiviral protein, of *A. viridis.*
Figure 3:
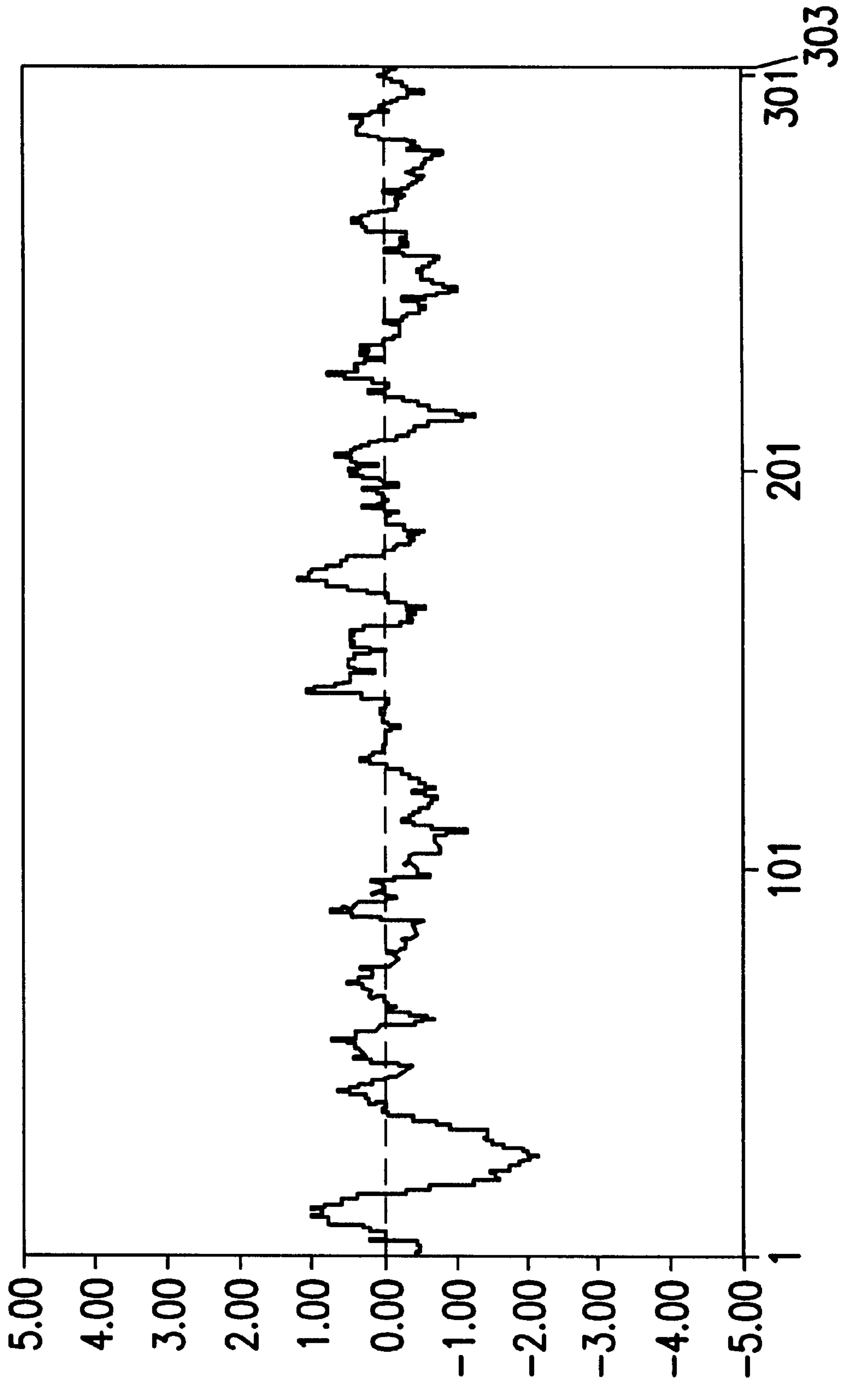
FIG. 3 is a diagram of the hydropathicity of amino acid sequence of amarandin-S.

The present invention relates to the isolated cDNA sequence encoding amarandin-S of *A. viridis*, ribosome-inactivating protein having antiviral activity, particularly the isolated nucleotide sequence of cDNA cloned in full length, to the expression vector containing said cDNA sequence and to a host transformed by said vector.

Ribosome-inactivating proteins (RIPs) are classified as type 1 and 2. Type 1 RIP has a unique enzymatic polypeptide chain with N-glycosidase activity on the ribosomal RNA that irreversibly impairs protein synthesis by enzymatically modifying the EF-2-dependent GTPase activity of the subunit. Type 2 RIP is consisting in two polypeptide chains linked by a disulfide bond, A-chain being the enzymatic chain able to attack the 60S ribosomal subunit and B-chain being a lectin able to recognize membrane sugars, mostly galactose residues. Type 1 RIPs are relatively abundant and to date nearly 30 have been isolated, the best known of which are saporin and the pokeweed antiviral protein. The pokeweed antiviral protein was shown to inhibit protein synthesis in the host cells. Subsequently it was found that both the toxins and the A-chain-like proteins, like the pokeweed antiviral protein (PAP), the wheat-germ inhibitor, the *Momordica charantia* inhibitor and gelonin, strongly inhibited eukaryotic ribosomes. Extacts from *Bryonia dioica* (bryony) seeds from *Dianthus caryophyllus* had strong inhibitory effect on protein synthesis. Type 2 RIPs, which can enter cells through the interaction of their lectin moiety with the cell membrane, are among the most potent natural toxins, the best known of which is ricin.

Although RIPs have similar physicochemical properties and seem to have identical effects on protein synthesis, ribosomes from various plants, protozoa and prokaryotes have different sensitivity patterns to RIP. For this reason, interest in RIPs stems from their potential utilization in medicine and agriculture area, due to their antiviral and antifungal activities.

We have cloned and expressed cDNA sequence coding for RIP 1 of *A. viridis*, amarandin-S. The isolated nucleotide sequence of amarandin-S is reported in the SEQ ID NO. 1.

The present invention relates to cDNA sequence encoding amarandin-S, eukaryotic ribosome-inactivating protein (RIP) having antiviral activity, which is present in *A. viridis*, to the expression vector containing said cDNA sequence and to a host transformed by said vector.

The isolated nucleotide sequence of cDNA (hereafter amarandin-S cDNA sequence), which is capable of encoding the full length amino acid sequence of amarandin-S, accessing antiviral activity, has been determined. Amarandin-S cDNA sequence was deposited at the GenBank (National Center for Biotechnology Information, National Library of Medicine, National Institute of Health, 9600 Rockville Pike, Bethesda, Md. 20892, USA) with the accession No. U70215. Amarandin-S has about 28% amino acid sequence homology with the pokeweed antiviral protein. Inventors also have identified the restriction enzyme sites in amarandin-S cDNA sequence and have provided the expression vector containing said cDNA sequence and a host transformed by said vector.

The isolated nucleotide sequence of amarandin-S cDNA encodes 32,000 molecular weight of protein with 284 amino acid residues, based on SDS-PAGE. According to its isolation from *A. viridis*, it was named amarandin-S. Isoelectric point of amarandin-S is remarkably basic (pI ~11). As little as 3 ng/ml of amarandin-S is inhibitory, amarandin-S is very effective inhibitory of ribosome function in vitro, apparently by interfering with EF-2 (elongation factor 2) mediated the translocation of the nascent peptide chain along the ribosome. This action is enzymatic, as the $IC_{50}$ (50% inhibitory concentration) for mammalian ribosome is of the order of $10^{-10}$ M. There was 95% decrease in the production of extracellular infectious virus when exogenous application of 0.5 g/ml amarandin-S mixed with tobacco mosaic virus on the upper surface of *Nicotiana glutinosa leaves*.

Within the context of the present invention, amarandin-S refers to the enzyme that mediates either the cleavage of N-glycosidic bond of a specific position in plant viral RNA or the inhibition of plant viral infection. The expression vector as used herein refers to a vector pLES97010 formed by ligation of the isolated amarandin-S cDNA sequence from *A. viridis*, which is capable of producing amarandin-S, into a plasmid pRSET.

In one embodiment of the present invention, the lambda UniZap II phage has been used as a cloning vector. cDNA library is constructed that is based upon mRNA sequence extracted from leaves of *A. viridis*. A first strand cDNA can be synthesized enzymatically using the isolated mRNA as a template, an oligo dT sequence as a primer and a reverse transcriptase as the enzyme. After the construction of the first strand cDNA, a second strand cDNA can be synthesized enzymatically using the first strand cDNA as a template and a DNA polymerase as the enzyme. In the present invention, the resulting double-stranded cDNA molecules are inserted into lambda UniZap II vector, to produce cDNA library.

The resulting cDNA library may be capable of expressing amarandin-S cDNA sequence in bacteria. Microbes containing amarandin-S cDNA sequence can be identified using antibodies to amarandin-S or alternatively, using a nucleic acid probe specific for amarandin-S cDNA sequence (hereafter amarandin-S cDNA specific probe). The transformed cells containing amarandin-S cDNA sequence can then be propagated, and large amounts of amarandin-S can be extracted.

Plant DNA or DNA from other organisms that hybridizes with a labelled nucleic acid probe specific for amarandin-S cDNA sequence can be identified and isolated. The isolated amarandin-S cDNA sequence can be ligated to a vector pRSET to produce the expression vector, pLES97010. The said expression vector containing said cDNA sequence can be used to transform a competent host, *E. coli* strain BL21 (DE3), and to induce the production of amarandin-S in said host. *E. coli* BL21(DE3) pLES97010 was deposited at Korean Collection for Type Cultures (KCTC), KRIBB, located at #52, Oun-dong, Yusóng-ku, Taejón 305-333, Republic of Korea, under accession No. KCTC 0343BP on Jun. 20, 1997.

A vector that is suitable for use in the context of the present invention can be a plasmid that is capable of being transferred into a host cell and of replicating in a host cell. In a preferred embodiment, a suitable vector is pLES97010 that is capable of carrying an insert of amarandin-S cDNA sequence in a non-essential region of pRSET.

A suitable transformed host is *E. coli* BL21(DE3) that is capable of expressing the amarandin-S cDNA sequence. In a preferred embodiment, said host is not capable of producing 32,000 molecular weight of amarandin-S in a significant amount before transformation, and becomes capable of producing amarandin-S in a significant amount after transformation.

In a preferred embodiment of the present invention, cDNA library, instead of a genomic DNA library , is constructed using mRNA isolated from *A. viridis*. Total RNA is obtained from *A. viridis* by conventional laboratory techniques, e.g., as in Krawetz et al., Biotechniques, 2:542–547, 1984 and Turpen et al., Biotechniques, 4:11–16, 1986, the contents of which are incorporated herein by reference.

The purification of mRNA herein was performed with a commercial kit (Oligotex mRNA midi kit, Qiagen Inc., USA). mRNA concentration is then determined spectrometrically.

The integrity of mRNA preparation, i.e., whether it is full length or simply a small fragment with a 3' poly A tail, is determined by in vitro translation of the mRNA. A full-length mRNA can be selected and used to construct cDNA library. The isolated amarandin-S cDNA sequence in this library can be detected utilizing either amarandin-S cDNA specific probe or antibodies if the cDNA library expresses said cDNA.

The plant material that is used for the isolation of mRNA is from *A. viridis* capable of synthesizing amarandin-S. For example, since Amaranthus seedlings produce amarandin-S from the very earliest stages of growth, mRNA capable of encoding amarandin-S can be obtained from Amaranthus seedlings. The isolated mRNA is then used as a template for synthesis of first strand cDNA molecules. The first-strand cDNA is, in turn, used as a template for a second-strand cDNA synthesis utilizing, e.g., DNA polymerase I. In this manner, cDNA library can be generated.

To find the nucleotide sequence in the cDNA library that is capable of encoding amarandin-S, a complementary nucleic acid probe can be used that contains a predicted nucleotide sequence based upon a known amino acid sequence of the amarandin-S protein. In the alternative, polyclonal or monoclonal antibodies to amarandin-S can be produced in experimental animals or in hybridomas, respectively, and used to identify the transformed host cell that produces amarandin-S.

In a preferred embodiment of the present invention, at least a portion of the amino acid sequence of the purified amarandin-S protein is determined by sequenceing. Nucleic acid probes based upon the predicted nucleotide sequence can be constructed in accordance with the conventional laboratory techniques. In formulating the sequence to be constructed, different strategies can be adopted.

DNA sequence from the clone that carries amarandin-S cDNA sequence and that reacts positively with the amarandin-S cDNA sequence specific probe can be isolated, and be ligated to another vector after removing the amarandin-S cDNA sequence. Removal of the amarandin-S cDNA sequence is accomplished by digesting cDNA from the original positive clone with an enzyme, e.g., EcoRI, that frees the Amaranthus cDNA from the vector. This method of gene removal is feasible because when the Amaranthus cDNA library is constructed, the cDNA is inserted into the proper vector at an EcoRI restriction site. Digestion of the vector that contains cDNA insert with EcoRI, therefore, frees the insert from the viral vector sequence.

In one embodiment of the present invention, the amarandin-S cDNA sequence can be subcloned in plasmid pRSET (i.e., the resulted vector is called as pLES97010) and maintained in *E. coli* strain BL21(DE3) for the production of large quantities of amarandin-S. The host cell transformed by said vector pLES97010 is propagated to produce large quantities of amarandin-S. Amarandin-S can be extracted from the transformed host in accordance with the conventional laboratory techniques.

Restriction map of amarandin-S cDNA sequence can be constructed by treating amarandin-S cDNA sequence with restriction enzymes, e.g., AccI, AflI, AluI, AlwI, AocI, AosI, ApyI, AspI, AsuI, BanI, BanII, BclI, BglI, BsmAI, BsmI, Bsp1286I, BspHI, BstBI, BstNI, BstXI, CfoI, CfrI, ClaI, DdeI, DpnI, DraI, DraII, Eco57I, EcoRI, EcoRV, Fnu4HI, FspI, GdiII, HaeI, HaeIII, HgiAI, HinP1I, HincII, HinfI, HphI, KpnI, Ksp632I, Ksp632I, MaeI, MaeII, MseI, MstI, NlaIII, NlaIV Nsp(7524)I, NspII, PleI, PpuMI, RsaI, SacI, Sau3AI, ScaI, SecI, SnaBI, SnaI, SplI, SstIII, TaqI, TspEI, and determining the size of the DNA fragments generated therefrom. Based upon the identity of the restriction enzymes that are capable of digesting the amarandin-S cDNA sequence and the size of the DNA fragments each of these enzymes generates, a restriction map of the amarandin-S cDNA sequence can be generated.

As described in the present invention, the isolated nucleotide sequence of cDNA for antiviral protein, amarandin-S, and its deduced amino acid sequence will provide the valuable informations on the further detailed structure-function relationship as well as understanding on the molecular action mechanism of RIPs against the viral infection. Therefore, the present invention is very important to inhibit virus replication comprising virus-induced human diseases, like HIV-1 replication, selectively in cell cultures. Also, the present invention can play a role in developing the broad spectrum of virus-resistance to the economically valuable crops, or to custom design extremely specific and very effective small peptide conferring an antiviral activity to interfere with the penetration stage of certain myxoviruses.

The following example is given by way of illustration to facilitate a better understanding of the present invention and is not intended to limit the scope thereof.

EXAMPLE 1

$NH_2$-Terminus Amino Acid Sequence Analysis

Amarandin-S was purified by the conventional column chromatography. The purified amarandin-S was subjected to SDS-PAGE in the presence of β-mercaptoethanol. Protein electroblotted onto PVDF membrane was detected by staining with 0.2% Coomassie Blue R-250 (w/v) in methanol-:water:acetic acid (50:40:10) for 3 min. The membrane was washed in methanol:water:acetic acid (48:47:5), and the protein band was cut out of the PVDF membrane and applied to Beckman 890C amino acid sequencer equipped with a Sequemat P-6 autoconverter. An Altex 345C HPLC and a Hewlett-Packard 3390A intergrator were used to analyze the products, according to the method of Tarr.

EXAMPLE 2

Isolation of mRNA from *Amaranthus viridis*

Ten grams of frozen *A. viridis* leaves were homogenized in mortar and pestle to a fine powder. The grounded material was added with 10 ml of ice cold extraction buffer (200 mM Tris-acetate, pH 8.0, 120 mM potassium acetate, 50 mM Mg-acetate, 0.04% DTT, 0.4% 2'-3' AMP), and the suspension was centrifuged at 4° C. for 20 min at 15,000 rpm. The supernatant fraction was collected. The pellet was re-extracted with 10 ml of the same buffer and the mixture was centrifuged as before to remove additional debris. The combined supernatant was then extracted twice with the same volume of a 1:1 phenol:chloroform solution. The extraction sequence was followed by a further extraction with chloroform and the mixture was centrifuged again. The obtained aqueous solution was added with ⅓ volume of 8 M LiCl and incubated overnight at 4° C. followed by the centrifugation. The precipitate was suspended with water. The obtained aqueous solution was added with 0.1 volume of 3 M Na-acetate, mixed and added with 2 volume of absolute ethanol. The resulting mixture was centrifuged at 10,000 rpm for 10 min at 4° C., and the precipitate was washed with 70% ethanol and centrifuged again. The precipitate was dried and resuspended in water. mRNA was then purified with a commercial kit (Oligotex mRNA midi kit, Qiagen Inc., USA). The so purified polyadenylated mRNA was precipiteated for overnight at 4° C. with 0.1 volume of Na-acetate and 2.0 volume absolute ethanol and centrifuged. The precipitate was washed with 70% ethanol and finally suspended water and stored at −80° C. 35 $\mu$g poly$A^+$mRNA were obtained from 1 mg of total RNA.

EXAMPLE 3

Synthesis of cDNA from *Amaranthus viridis* cDNA library from *A. viridis* was constructed with Uni-ZAP™ cDNA library kit (Stratagene, USA), according to the manufacturer's manual. The first-strand cDNA was synthesized from the reaction mixtures of 5 $\mu$g of poly-$A^+$ RNA, oligo $(dT)_{12}$-$_{18}$, murine reverse transcriptase, dNTP, BSA, and DTT. In order to synthesize double-stranded cDNA, the first-strand cDNA synthesized was blunted at cDNA termini with the addition of *E. coli* RNase H, *E. coli* DNA polymerase I, and dNTP at 16° C. for 3 h followed by treating the dNTP mixture with Pfu DNA polymerase at 65° C. for 10 min.

EXAMPLE 4

Ligation of cDNA into Uni-ZAFT™ vector

The termini of cDNA synthesized were ligated to the EcoRI adapter for the insertion of cDNA to the vector. cDNA synthesized was reacted with the addition of EcoRI adapter, ATP, T4 DNA ligase at 12° C. overnight followed by further reaction with the addition of T4 DNA kinase and ATP at 37° C. for 30 min. cDNA was purified with Sephacryl S-500 spin column, and its signal was confirmed on 1.0% agarose gel electrophoresis. Above 1 kb of cDNA fractions was used for further experiments. The insertion of cDNA was resulted from the reaction of the mixtures containing 200 ng of cDNA, 1 $\mu$g of vector DNA (Stratagene) and T4 DNA ligase at 4° C. for 48 h.

EXAMPLE 5

Construction and the Amplification of cDNA Library

Gigapack II packaging extract was reacted by the addition of recombinant vector at 22° C. for 2 h. The reaction solution was adjusted up to 500 $\mu$l of final volume with SM buffer supplemented with 10 $\mu$l of chloroform, and was immediately used or stored at 4° C. until it will be used. Total plaque-forming unit (pfu) of cDNA library was obtained from $10^2$–$10^6$ fold diluted solution. Two hundreds $\mu$l of *E.*

*coli* strain XL1-Blue MRF' were incubated with cDNA library at 37° C. for 15 min, and plated to reach $10^6$ pfu on plate of 150 mm in diameter. The plate supplemented with 5 ml of SM buffer was incubated at 4° C. overnight after incubated the plate at 37° C. for 12 h. The supernatants was obtained from the reacted SM buffer by centrifuging at 12,000 rpm for 10 min, and stored with 100 μl of chloroform at −4° C. The plaque-forming unit was calculated as described in the above.

EXAMPLE 6

Cloning of Partial Amarandin-S cDNA

Two separate degenerate primers were designed based on the N-terminus 8 amino acid sequence SEQ ID NO. 2 (5'-ATGAAGAAGGTTTTAGGAGG AGGA-3') and the consensus peptide sequence of prereported RIPs SEQ ID NO. 3 (5'-GAGGCAGCRMGRTTCAAGTACAT-3')(see LANE 2 IN FIG. 1). The sequences of the degenerate primer for the consensus peptide sequence of prereported RIPs was designed as following:

primer (SEAA): 5'-GAG GCA GCR MGR TTC AAG TAC AT-3' (SEQ ID NO. 3)

which R is indicating for A to G and M for A or C.

Total cDNA library 5 μl (equivalent $5\times10^8$ pfu), were used in a 50 μl reaction mixture containing 20 μM of primers and T3 or T7, 0.2 mM dNTP's, 1.5 mM $MgCl_2$, 10 mM Tris, pH 8.3, and 50 mM KCl. The samples were overlaid with a drop of sterilized mineral oil to minimize the evaporation. To perform hot start PCR, the samples were heated at 95° C. for 5 min and then 2.5 units of Taq polymerase were added. After this prerun, 30 cycles of amplifications were carried out at 30 sec 94° C., 30 sec 45° C., and 30 sec 72° C. From the PCR products, 10 μl of aliquots were mixed with 2 μl of 6x loading buffer and separated on a 1% Agarose gel.

*A. viridis* cDNA library was used as template for PCR. Based on the above degenrate PCR primers, 450 base pairs long fragment was expected under high stringency PCR (FIG. 1). On the agarose gel the product was shown as a band in the expected size range. The Purified PCR products were then subcloned in to pGEM T-vector plasmid (Promega) without additional enzymatic modification, and plated on LB agar plates overnight. The use of T-vector allows the blue color selection for insert bearing clones.

EXAMPLE 7

Sequencing of PCR Product of Partial Amarandin-S cDNA

All of the positive clones were picked up using a toothpick and inoculated in 2 ml of LB/amp overnight at 37° C. Samples were spun at 14,000 rpm for 30 sec at 4° C. Plasmid DNA was prepared using Qiagene Miniprep kit (Qiagen). Isolated DNA samples were digested with Pst I and Nco I to cut out the inserts to compare their sizes. Sequenase version 2.0 $T_7$ DNA polymerase sequencing protocol (USB) was used for nucleotide sequencing analysis. The samples were then separated on 6% acrylamide gel at constant power 65 W for the time required to get optimal resolution of the sequence of interest. After running, the gel was placed on a piece of 3MM paper and covered with Saran wrap. The gel was then dried for 30 min at 80° C. under vacuum drier (Bio-Rad) and exposed to Kodak X-Omat film overnight at RT. The sequence of the sample was read and analyzed using GCG Sequencing Analysis Program. BlastN (NCBI, NLM, NIH) search shows that all clones have high sequence homologies to other RIPs.

EXAMPLE 8 cDNA Library Screening

Once nucleotide sequence was checked, the clone was grown in a 100 ml culture, and plasmid DNA was prepared using the Maxi-prep kit (Qiagen). Insert was isolated by digesting with restriction enzymes of Pst I and Nco I from plasmid DNA. The sample was separated on a 1% Agarose gel and the insert was isolated using Qiaquick gel extraction kit (Qiagen). Isolated insert was labeled using a Multiprime DNA Labeling Kit (Amersham). The labeled DNA was separated using Nuctrap probe purification column chromatography (Stratagene). The effluent was transfered to a new Eppendorf tube. Incorporation rate of the labeled nucleotide was calculated by measuring the radioactivity of 1 μl of sample before and after passing through the column. The labeled DNA was used as a probe to screen cDNA library.

Lambda UniZap II phages containing Amaranthus cDNA library were plated at a appropriate numbers and transfered to the Nitrocellulose membranes (Hybond$^+$, Amersham). After 1 min, the filters were lifted and placed on a piece of 3MM paper wetted in Denaturing solution for 5 min. The filters were soaked in the Neutralizing solution for 5 min and then rinsed briefly in 2×SSC and dried on 3MM paper at RT. Air dried filters were then sandwitched between 3MM papers and baked in oven at 80° C. for 2 hours to fix the DNA. Filters were transferred to a siliconized glass bottle containing 5 ml of prehybridization solution and incubated for 2 hours at 58° C. Amersham Hybridization Oven. One million counts per minute (cpm) of preheated radio-labeled probe was added in every mililiter of prehybridization solution to each bottle and then incubated overnight at 64° C. When the hybridization was completed, the filters were washed in high stringency condition and the background signal was checked with Geiger counter. After a number of washes, the filters were briefly rinsed with 0.1×SSC/0.1% SDS and then dried on 3MM paper and wrapped with Saran wrap. The wrapped filters were placed in an X-ray film holder. A sheet of film (Kodak X-omat AR) and a calcium-tungstate-phosphorscreen (Dupont Cronex Lightning-Plus) were laid on the filters and exposed at −80° C.

EXAMPLE 9 cDNA Sequencing

All the positive plaques were picked up by aligning the film and plates and suspended in 500 μl of SM containing a drop of chloroform. Aliquots of each picked clone were pooled and replated on LB/tetracyclin plates for secondary screening. For this, duplicates of filters were prepared and well-isolated coincident plaques were picked and the insert were sequenced.

EXAMPLE 10

Expression of cDNA in *E. coli*

The amarandin-S cDNA insert was ligated to pRSET-vector for the construction of the expression vector at 12° C. overnight. The said expression vector was named as pLES97010. The ligation mixture and 50 μl of *E. coli* strain BL21(DE3) cells were incubated on ice for 30 min, followed by heating at 42° C. for exactly 60 sec. The tube was immediately chilled on ice for 2 min. The 450 μl of SOC were added and incubated at 37° C. for 1 hour at 250 rpm in the orbital shaker. A quarter of mixture was plated on Amp plate, and the plate was incubated at 37° C. overnight. The transformed *E. coli* strain BL21(DE3) cells were cultured in 10 ml of LB broth containing 100 μg/ml of ampicillin to an $OD_{600}$ of 0.6. The culture was then induced with 1 mM IPTG for 3 h at 37° C. The sonicated cells were centrifuged at 3,000 rpm for 15 min at 4° C. to extract soluble proteins. The supernatant was centrifuged at 100,000 g for 1 h at 4° C. The supernatant, containing soluble proteins, was recovered and the pellet of insoluble proteins was resuspended in 10 mM Tris-HCl, pH 8.0, and 5 mM EDTA.

Two solutions were analyzed by SDS-PAGE and immunoblot, and the presence of a band of about 32,000 daltons of molecular weight corresponding to recombinant amarandin-S was confirmed.

EXAMPLE 11

Restriction Mapping of Amarandin-S cDNA Sequence

Restriction mapping of the amarandin-S cDNA sequence was predicted by DNAsis. A restriction map of the amarandin-S cDNA sequence is shown in FIG. 2. In FIG. 2, the numbers in parentheses represent the size of the restriction fragments produced by each restriction endonuclease. Restriction enzymes involved in amarandin-S DNA sequence have been estimated as AccI, AflI, AluI, AlwI, AocI, AosI, ApyI, AspI, AsuI, BanI, BanII, BclI, BglI, BsmAI, BsmI, Bsp1286I, BspHI, BstBI, BstNI, BstXI, CfoI, CfrI, ClaI, DdeI, DpnI, DraI, DraII, Eco57I, EcoRI, EcoRV, Fnu4HI, FspI, GdiII, HaeI, HaeIII, HgiAI, HinP1I, HincII, HinfI, HphI, KpnI, Ksp632I, Ksp632I, MaeI, MaeII, MseI, MstI, NlaIII, NlaIV Nsp(7524)I, NspII, PleI, PpuMI, RsaI, SacI, Sau3AI, ScaI, SecI, SnaBI, SnaI, SplI, SstIII, TaqI, TspEI. The both end of amarandin-S cDNA sequence are defined by enzymes VspI and SacI, respectively.

REFERENCES

James B. Hudson, ANTIVIRAL COMPOUNDS from PLANTS, 1990, CRC Press, Inc.

Krawetz et al., Biotechniques, 1984, 2:542–547.

Turpen et al., Biotechniques, 1986, 4:11–16.

Maniatis et al., Molecular Cloning:A Laboratory Manual, Cold Spring Harbor, 1989.

Lorenzetti et al., 1996, U.S. Pat. No. 5,529,932.

Legname et al., 1996, U.S. Pat. No. 5,501,970.

---

What is claimed is:

1. The isolated nucleotide sequence of cDNA (GenBank No. U70215) encoding for a ribosome-inactivating protein, amarandin-S, from *A. viridis* as shown in SEQ ID NO. 1.

2. A cloning vector comprising said cDNA sequence in claim 1.

3. An expression vector comprising said cDNA sequence as claimed in claim 1.

4. The vector according to claim 3, wherein said vector is the plasmid pLES97010 obtainable from the *E. coli* strain, KCTC No. 0343BP.

5. A host cell transformed by the vector as claimed in claim 4 (*E. coli* strain, KCTC No. 0343BP).

6. The isolated cDNA sequence according to claim 1, wherein said cDNA sequence comprises the restriction site for each enzyme: AccI, AflI, AluI, AlwI, AocI, AosI, ApyI, AspI, AsuI, BanI, BanII, BclI, BglI, BsmAI, BsmI, Bsp1286I, BspHI, BstBI, BstNI, BstXI, CfoI, CfrI, ClaI, DdeI, DpnI, DraI, DraII, Eco57I, EcoRI, EcoRV, Fnu4HI, FspI, GdiII, HaeI, HaeIII, HgiAI, HinP1I, HincII, HinfI, HphI, KpnI, Ksp632I, Ksp632I, MaeI, MaeII, MseI, MstI, NlaIII, NlaIV Nsp(7524)I, NspII, PleI, PpuMI, RsaI, SacI, Sau3AI, ScaI, SecI, SnaBI, SnaI, SplI, SstIII, TaqI, TspEI.

* * * * *